(12) United States Patent
Obradovic et al.

(10) Patent No.: US 11,642,499 B2
(45) Date of Patent: May 9, 2023

(54) BALLOON CATHETER

(71) Applicant: Bentley InnoMed GmbH, Hechingen (DE)

(72) Inventors: Milisav Obradovic, Lorrach (DE); Rainer Bregulla, Balingen (DE)

(73) Assignee: Bentley InnoMed GmbH, Hechingen (DE)

( * ) Notice: Subject to any disclaimer, the term of this patent is extended or adjusted under 35 U.S.C. 154(b) by 0 days.

(21) Appl. No.: 15/748,146

(22) PCT Filed: Jul. 29, 2016

(86) PCT No.: PCT/EP2016/068184
§ 371 (c)(1),
(2) Date: Jan. 26, 2018

(87) PCT Pub. No.: WO2017/017259
PCT Pub. Date: Feb. 2, 2017

(65) Prior Publication Data
US 2018/0221630 A1    Aug. 9, 2018

(30) Foreign Application Priority Data

Jul. 29, 2015 (DE) ..................... 10 2015 112 390.8

(51) Int. Cl.
*A61M 25/10* (2013.01)
*A61F 2/958* (2013.01)
(Continued)

(52) U.S. Cl.
CPC ............ *A61M 25/1002* (2013.01); *A61F 2/04* (2013.01); *A61F 2/856* (2013.01); *A61F 2/958* (2013.01);
(Continued)

(58) Field of Classification Search
CPC ........ A61F 2002/065; A61F 2250/0039; A61F 2/958; A61F 2/856; A61M 25/1002;
(Continued)

(56) References Cited

U.S. PATENT DOCUMENTS 4,744,366 A * 5/1988 Jang ................... A61M 25/1011
604/101.02
4,795,427 A * 1/1989 Helzel ................ A61M 25/1011
604/9
(Continued)

FOREIGN PATENT DOCUMENTS

CN      102416218 A    4/2012
JP      63-132667      6/1988
(Continued)

OTHER PUBLICATIONS

Office Action dated Nov. 14, 2019 in connection with related Russian Patent Appl. No. 2018107043/14.
(Continued)

*Primary Examiner* — Alexander J Orkin
(74) *Attorney, Agent, or Firm* — Brooks Kushman P.C.

(57) ABSTRACT

The invention relates to a balloon catheter, in particular for the widening of stents in fenestrations and for T-branch protheses, being provided with a balloon (4), a supply line in the catheter (2) leading to the balloon (4), which allows the balloon (4) to be pressurized, and a central lumen (3) for a guidewire, with the balloon (4) in the expanded state having at least two areas (P, D, M) of different diameter, with these areas merging into one another by forming a step.

2 Claims, 3 Drawing Sheets

Figure 5:
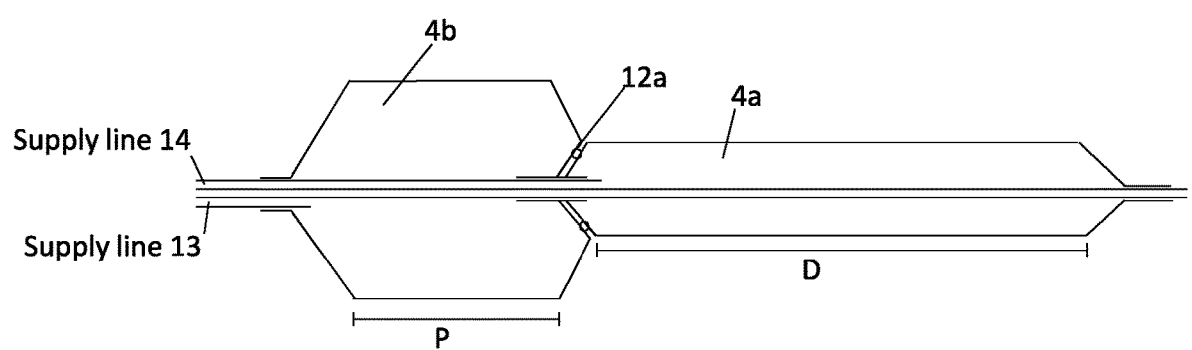

(51) Int. Cl.
    *A61F 2/856*         (2013.01)
    *A61F 2/04*           (2013.01)
    *A61M 27/00*        (2006.01)
    *A61M 29/02*        (2006.01)
    *A61F 2/82*           (2013.01)
    *A61F 2/95*           (2013.01)
    *A61F 2/06*           (2013.01)

(52) U.S. Cl.
    CPC .... *A61M 25/1011* (2013.01); *A61M 25/1018* (2013.01); *A61M 27/002* (2013.01); *A61M 29/02* (2013.01); *A61F 2/9522* (2020.05); *A61F 2002/065* (2013.01); *A61F 2002/821* (2013.01); *A61F 2250/0039* (2013.01); *A61M 2025/1013* (2013.01); *A61M 2025/1045* (2013.01); *A61M 2025/1059* (2013.01); *A61M 2025/1072* (2013.01)

(58) Field of Classification Search
    CPC .. A61M 2025/1045; A61M 2025/1059; A61M 27/002; A61M 25/1018
    See application file for complete search history.

(56) References Cited

U.S. PATENT DOCUMENTS

| | | | | |
|---|---|---|---|---|
| 4,896,670 | A * | 1/1990 | Crittenden | A61M 25/1002 604/103.1 |
| 5,609,605 | A * | 3/1997 | Marshall | A61F 2/07 606/191 |
| 5,843,116 | A * | 12/1998 | Crocker | A61M 25/1002 606/192 |
| 6,419,685 | B2 * | 7/2002 | Di Caprio | A61M 25/104 604/101.02 |
| 6,488,653 | B1 * | 12/2002 | Lombardo | A61M 25/1002 604/101.01 |
| 6,669,711 | B1 * | 12/2003 | Noda | A61B 17/12104 604/907 |
| 6,719,720 | B1 * | 4/2004 | Voelker | A61F 2/958 604/99.02 |
| 7,862,601 | B2 | 1/2011 | Sanati et al. | |
| 10,806,616 | B2 * | 10/2020 | Bregulla | A61M 25/1011 |
| 2002/0120320 | A1 | 8/2002 | Wang et al. | |
| 2004/0073250 | A1 * | 4/2004 | Pederson, Jr. | A61F 2/958 606/192 |
| 2005/0043679 | A1 * | 2/2005 | Devens, Jr. | A61M 25/1002 604/103.06 |
| 2005/0055043 | A1 * | 3/2005 | Foltz | A61M 29/02 606/193 |
| 2005/0209674 | A1 * | 9/2005 | Kutscher | A61M 25/1002 623/1.11 |
| 2006/0004323 | A1 * | 1/2006 | Chang | A61F 2/82 604/28 |
| 2006/0265041 | A1 * | 11/2006 | Sanati | A61F 2/90 623/1.11 |
| 2007/0129749 | A1 * | 6/2007 | Thomas | A61M 25/1011 606/194 |
| 2007/0185562 | A1 * | 8/2007 | Furst | A61F 2/82 623/1.15 |
| 2007/0270935 | A1 * | 11/2007 | Newhauser | A61F 2/958 623/1.11 |
| 2008/0109056 | A1 * | 5/2008 | Chalekian | A61F 2/954 623/1.11 |
| 2008/0183273 | A1 * | 7/2008 | Mesana | A61F 2/2433 623/1.11 |
| 2008/0319415 | A1 * | 12/2008 | Shturman | A61M 25/104 604/509 |
| 2011/0172690 | A1 * | 7/2011 | Cohn | A61B 17/32053 606/170 |
| 2011/0275990 | A1 | 11/2011 | Besser et al. | |
| 2014/0276585 | A1 * | 9/2014 | Gianotti | A61M 25/1002 604/99.01 |
| 2014/0277062 | A1 | 9/2014 | Pepper et al. | |
| 2014/0336569 | A1 * | 11/2014 | Gobel | A61M 3/0295 604/42 |
| 2014/0336741 | A1 * | 11/2014 | Connor | A61F 2/958 623/1.11 |
| 2018/0303645 | A1 * | 10/2018 | Bregulla | A61F 2/954 |

FOREIGN PATENT DOCUMENTS

| | | |
|---|---|---|
| JP | 2001-9037 A | 1/2001 |
| JP | 2008-541872 A | 11/2008 |
| JP | 2011-507671 A | 3/2011 |
| RU | 2491038 C2 | 8/2013 |
| WO | WO97/17101 A1 | 5/1997 |

OTHER PUBLICATIONS

Chinese Office Action dated Mar. 4, 2020 issued in related Chinese Patent Appl. No. 201680047293.6.

Japanese Office Action dated May 26, 2020 in connection with related Japanese Appl. No. 2018-504661.

Israeli Office Action dated Apr. 27, 2021 in connection with related Israeli Appl. No. 257183.

Indian Office Action dated Nov. 16, 2021 in connection with related Indian Appl. No. 201847003210.

\* cited by examiner

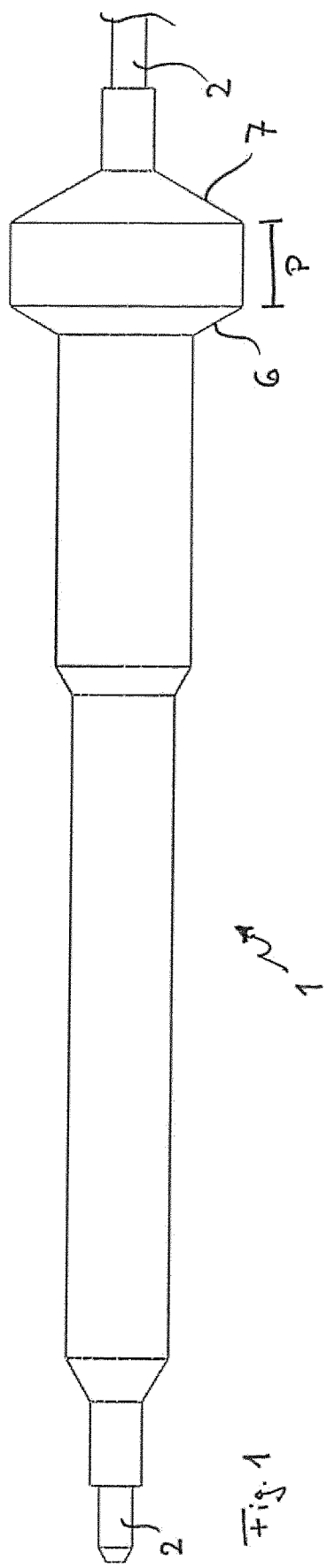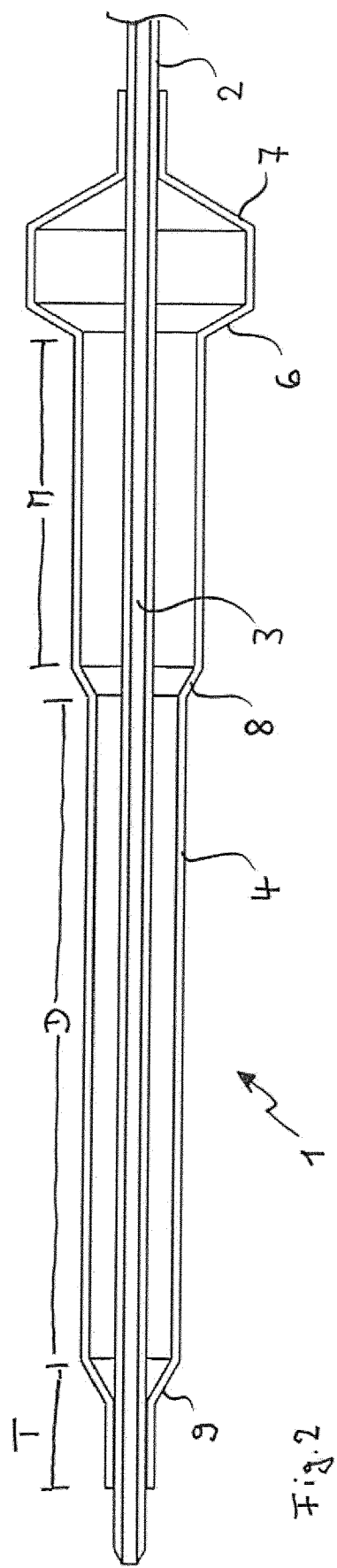

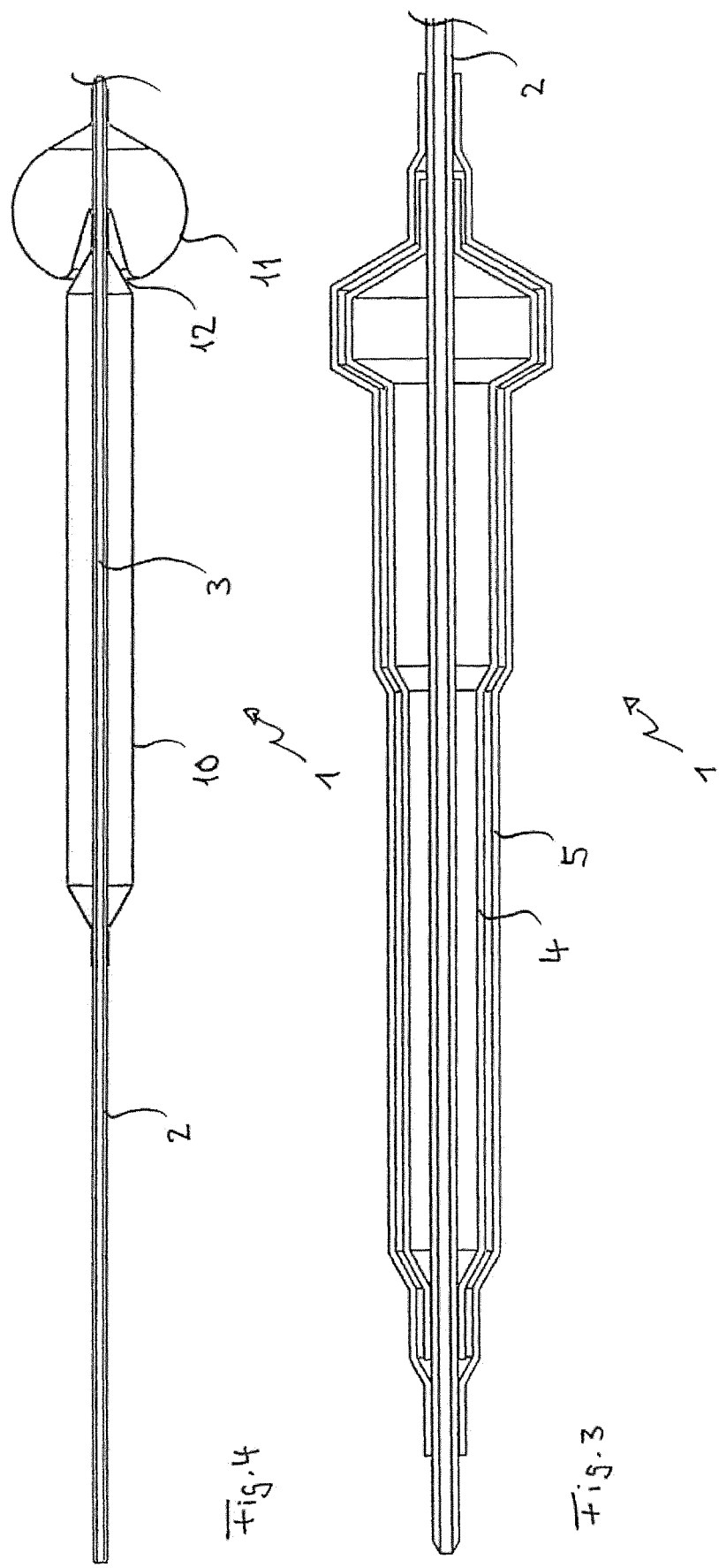

BALLOON CATHETER

The invention relates to a balloon catheter, in particular for widening stents in fenestrations, for T-branch prostheses and for shunts, with a stepped balloon, a supply line in the catheter to the balloon that allows the balloon to be pressurized, and a central lumen for a guidewire.

Balloon catheters have been used for many years to widen stents in vessels. For the purpose of widening stents, a stent is crimped onto the balloon catheter, dilated and placed at the desired implantation site with the help of a balloon catheter. Following this, the balloon catheter is removed from the vessel without the stent.

Stents are also placed with the help of balloon catheters in connections between two blood vessels (so-called shunts), for example in the liver when a TIPS (Transjugular Intrahepatic Portosystemic Shunt) is applied in the case of narrowing of the portal vein or hypertension in the liver.

In angioplasty, balloon catheters are used for widening a narrowed vessel mechanically and press plaques that have formed there against the vessel wall.

A special problem arises when, aside from the main branch, also the branching vessel must be provided with a stent in the area of vascular bifurcations. In this case, a stent fitted with a fenestration is first arranged in the main branch, where it is implanted in such a way that the window is positioned in the area of the junction. Afterwards, another stent is inserted into the branching off vessel, dilated there and adapted to the stent arranged in the main branch by widening. As a rule, this requires several separate steps, in particular if the branching off vessel narrows in its course and a stepped widening has to be accomplished. In addition, the stent in the side branch has to be adjusted and matched to suit the window and the stent configuration in the main branch.

For this adjustment it is possible to proceed in steps using several balloons of different diameters which are placed in position one after the other. However, a so-called "balloon in the balloon" may also be employed, in which two balloons are coupled to each other in such a way that they can be pressurized separately and be used to achieve different expansion volumes. However, disadvantageous is the effort involved in using several separate balloons.

It is the objective of the invention to provide a balloon catheter by means of which stents can be precisely placed in branching vessels or shunts and, if necessary, also connected to a stent with a fenestration placed in the main branch taking into account a narrowing diameter of the branching vessel.

This objective is reached with a balloon catheter of the kind first mentioned above, in which the balloon in the expanded state has at least two areas of different diameter, with these areas merging into each other while forming a step.

The balloon catheter proposed by the invention is provided with a catheter shaft, a stepped balloon, a lumen for applying pressure to the balloon as well as a lumen for a guidewire. The balloon itself is of stepped design, in such a way that at least one area has a diameter that is enlarged in comparison to another area. In this context, stepwise design means that the individual segments, such as the proximal and distal areas, merge with each other by forming a step, whereby the such a gradation takes place in a relatively narrow range.

The balloons of the inventive balloon catheters have two or more areas of different diameter. For example, the proximal area may have a larger diameter than the distal area, which is advantageous for the placement of stents in the side branches of a main vessel. In principle, however, the distal area can also be enlarged in relation to the proximal area, which makes it easier to place a stent in a side branch, for example, if access is provided via this side branch. In this case, the enlarged portion of the balloon is placed in the main vessel in the outgoing area of the side vessel and thus allows the stent to be expanded in the entry area of the side vessel.

In addition, balloon catheters according to the invention can also have several stepped zones over the entire length, which is advantageous in the case of narrowing vessels, for example, or if there is a central area with a reduced diameter compared to the proximal and distal area. The latter variant is suitable, for instance, for the placement of stents in shunts, for example in the TIPS system, where it is important to fit the stent precisely into the shunt and at the same time not to expand too far in order to achieve flow regulation.

On the one hand, the inventive balloon catheter can be used to dilate vessels without stents to be placed in the process, and on the other hand for the placement of stents. The stents are crimped onto the balloon for this purpose, whereby the stents may extend over the entire length of the balloon, or reach over a partial stent area only. For example, when a stent is placed in a branch of a vessel, the stent is crimped onto the balloon in such a way that it protrudes into the area of the stepping so that it is enlarged forming a trumpet-like shape when the balloon is expanded at this end, thus enabling it to adapt to the wall of the main vessel or a stent placed in a main vessel.

The areas of the balloon of the inventive balloon catheter represent individual segments that correspond to the steps. These segments may have a connection with each other or be separated from one another by walls.

For example, the balloon may have an extended proximal and a reduced distal area. The distal region is kept rather slim. It can have an even diameter over its length, but may also become narrower towards the distal end of the catheter to allow adaptation to narrowing side branches.

The proximal area of the balloon in the balloon catheter provided according to the invention has a diameter that is considerably larger than in the distal area. In particular, the diameter is increased by about 50 to 100%.

Between the proximal and distal areas of the balloon, there may be a middle section having a diameter that ranges between the diameter of the proximal and distal areas. In such a case, the balloon has three steps. A fourfold stepping is possible as well, with the diameters of the individual segments decreasing from the proximal to the distal end.

As a rule, the balloon of this variant has a diameter (in expanded state) ranging between 5 and 14 mm in the proximal region, while the diameter in the distal region is between 2 and 6 mm.

In the event the proximal region of the balloon is enlarged, it shows a relatively steep rise on its flanks that, preferably, is evenly formed on both sides, i.e. the rise from the catheter shaft on the one hand and the rise at the proximally situated part of the balloon on the other hand. Expediently, the rise ranges between 45 and 75° in relation to the axis of the catheter. A steep rise in the enlarged zone is to be seen positive for the trumpet-like widening of the stent in the entry area of the branching vessel and conducive to the adaptation to the stent placed in the main branch, resp. to the main vessel from which the branch originates.

The same applies in the event that the diameter of the distal portion of the balloon is enlarged beyond that of the proximal part, and likewise, if the distal and proximal parts are enlarged in relation to the central portion.

The balloon of the inventive balloon catheter may thus be divided into several segments, with each segment having a separate supply line for the purpose of pressurization. The individual segments can be single balloons, which are located directly adjacent to neighboring single balloons. Expediently, the individual balloons are combined in this case.

The individual segments appropriately correspond to the above mentioned proximal, distal and, if applicable, middle areas, i.e. coincide with the individual steps. If single balloons are used, they are glued or welded together, preferably by spot-welding, at the points of contact, i.e. at the locations where the steps are arranged. The connection or junction of the individual balloons is important for an even expansion.

When using the balloon catheter according to the invention with enlarged proximal area divided into several segments or single balloons, particularly the distal region is dilated initially to enable the stent to be placed, then, if applicable, the middle area, and finally the proximal area which requires the greatest widening and in which the stent is to be adapted to the fenestration of the stent in the main branch or to the shape of the bifurcation in the area of the branch. If a single balloon is provided without any subdivision into individually dilatable segments, the dilatation takes place uniformly over the entire length.

Basically, it is possible to surround the balloon catheter with an external balloon that is closely arranged to the inner balloon or single balloons below. In this case, the external balloon is provided with a safety function according to one variant, i.e. it is not dilated separately, but expands together with the expansion of the balloon underneath or of its segments or balloons. Alternatively, and with a view to effecting pre-expansion, it is also possible to dilate the external balloon, followed by the final expansion which takes place via the inner balloon. In any case, the contours of the external balloon and the inner balloon or the inside balloon segments or balloons are provided so as to coincide with each other.

The inventive balloon catheter is manufactured in the customary way, and the materials are also commonly used materials in this field. The difference to the state of the art solely concerns the design of the balloons.

For the balloons, materials that are commonly adopted for this purpose can be employed. Preferably, a material with limited extensibility (non-compliant) is used for the inner balloon, such as polyamide 12, PET, nylon, and for the external balloon a well extensible (compliant or semi-compliant) material such as silicone rubber, Pebax, PA 11 or a mixture of Pebax and PA 11.

The invention is explained in more detail by way of the enclosed figures, where

FIG. 1: is an overall view of a balloon catheter proposed by the invention;

FIG. 2: shows a sectional view of the balloon catheter depicted in FIG. 1;

FIG. 3: illustrates a second variant of an inventive balloon catheter as a sectional view; and FIG. 4: is a sectional representation of a double balloon for TIPS applications.

FIG. 5: shows the proximal and distal areas, spot welds, and supply lines of another variation of the balloon catheter.

FIG. 1 shows an inventionally designed balloon catheter 1 with the distinctly widened proximal region P with steep flanks 7 extending towards the catheter and 6 towards distal region D, the relatively slender distal region D, which decreases in steps to the catheter diameter. The catheter 2 leads through the balloon structure 4 and terminates distally of the balloon structure 4.

For use, a stent is crimped onto the balloon catheter, said stent being widened through the expansion of the balloons and placed in a blood vessel. The illustration shows catheter 1 with balloon in expanded state.

FIG. 2 is a sectional representation of the balloon catheter 1 according to FIG. 1 showing catheter 2, a free lumen 3 for a guidewire used for placement of the catheter, and balloon 4.

The balloon 4 is subdivided into the proximal area P, distal area D, middle area M, and terminal area T. As shown by each of the Figures, the balloon segments are serially connected.

The proximal area P is significantly enlarged in comparison with the distal area D. The diameters of the middle area M are reduced in comparison to the diameter of proximal area P, but are still larger than the diameter of distal area D. The transitions from the proximal area P to the middle area M and from the middle area M to the distal area D as well as in the terminal area T are formed by the arrangement of relatively steep flanks 6, 8 and 9. Flank 6 is decisive for the adaptation of a stent to the fenestration of a stent in the main branch or for the adaptation to the vessel wall in the main branch during placement of the stent.

In the terminal area T, the balloon slims down and seals off tightly before the end of catheter 2. The channels which serve to fill the balloons with fluid are conventional and not shown in the drawing.

In FIG. 3 a variant of the inventive double balloon is illustrated in which the balloon 4 is surrounded by an external balloon 5. The external balloon 5 ensures greater safety and, in the event there is a separate expansion via another lumen, allows a more precise and targeted widening and adaptation of a stent to the configuration of the vessel. Otherwise, the balloon 1 shown in FIG. 3 corresponds to the representation in FIG. 2.

FIG. 4 shows a balloon catheter 1 for TIPS procedures, provided with a proximal balloon 11 of enlarged diameter and a distal balloon 10 of smaller diameter. Both balloons can be expanded separately, as required to carry out TIPS procedures in the liver. Both balloons are connected to each other via adhesive or weld spots 12, so that they form a unit when they are expanded. Not shown are the lumina which are used for the separate filling of the balloons. The figure shows lumen 3 intended to accommodate a guidewire for the placement of the device 1.

In another variation as shown in FIG. 5, the proximal segment P of the balloon (4b) is enlarged by 50% to 100% relative to the distal segment D of the balloon 4a. FIG. 5 also includes spot welds 12a and a supply line 13 for inflation of the proximal segment P of the balloon (4b) and supply line 14 for inflation of the distal segment D of the balloon 4a.

It goes without saying that there are numerous variations in the design of the proximal and distal areas. According to one variant, the proximal area has a more spherical shape. The distal area is shown to be of the same diameter, but it is of course also possible to provide for a further stepping or slimming towards the terminal end of the catheter. The diameter of the distal area, for example, may be reduced by 40% over its length towards the terminal end, and this slimming down can be brought about continuously or in steps.

The invention claimed is:

1. Balloon catheter, for TIPS procedures, being provided with a balloon, supply lines in the catheter leading to the balloon, which allow the balloon to be pressurized, and a central lumen for a guidewire, wherein the balloon in its expanded state is subdivided into at least two segments, each segment having a separate supply line for pressurization purposes and wherein the at least two segments of the balloon are of different diameter and longitudinally spaced along a longitudinal axis of the balloon catheter, with these at least two segments merging into one another by forming a step, characterized in that the balloon comprises first and second segments comprising opposing walls that are non-sharing and that the segments are serially connected to each other via individual weld spots located on and between said opposing walls and that the first segment has a spherical-like shape and has a diameter that is enlarged by 50% to 100% relative to the diameter of the second segment.

2. The balloon catheter of claim 1 with a crimped-on stent.

* * * * *